United States Patent [19]
Kreutner et al.

[11] Patent Number: 5,869,479
[45] Date of Patent: Feb. 9, 1999

[54] TREATMENT OF UPPER AIRWAY ALLERGIC RESPONSES

[75] Inventors: William Kreutner, West Paterson; John A. Hey, Nutley, both of N.J.

[73] Assignee: Schering Corporation, Kenilworth, N.J.

[21] Appl. No.: 909,319

[22] Filed: Aug. 14, 1997

Related U.S. Application Data

[60] Provisional application No. 60/023,416, Aug. 16, 1996.

[51] Int. Cl.$^6$ .......................... A61K 31/44; A61K 31/55
[52] U.S. Cl. ...................... 514/212; 514/220; 514/226.2; 514/255; 514/264; 514/290; 514/296; 514/322; 514/324; 514/326; 514/343; 514/352; 514/357; 514/397; 514/400; 514/849
[58] Field of Search ..................................... 514/290, 357, 514/212, 220, 226.2, 849, 255, 264, 296, 322, 324, 326, 243, 352, 397, 400

[56] References Cited

U.S. PATENT DOCUMENTS

| | | | |
|---|---|---|---|
| 2,567,245 | 9/1951 | Sperber et al. | 260/296 |
| 4,282,233 | 8/1981 | Vilani | 424/267 |
| 5,019,591 | 5/1991 | Gardner et al. | 514/461 |
| 5,217,986 | 6/1993 | Pomponi et al. | 514/400 |
| 5,352,707 | 10/1994 | Pomponi et al. | 514/651 |

FOREIGN PATENT DOCUMENTS

| | | | |
|---|---|---|---|
| 2207865 | 2/1989 | United Kingdom | A61L 15/03 |
| WO 94/18961 | 9/1994 | WIPO | A61K 31/13 |

OTHER PUBLICATIONS

R.W.S. Hew et al., "Characterization of Histamine H$_3$–Receptors in Guinea–Pig Ileum with H$_3$–Selective Ligands," *British Journal of Pharmacology*, vol. 101, pp. 621–624 (1990).

C.E. Tedford et al., "Pharmacological Characterization of GT–2016, A Non–Thiourea–Containing Histamine H$_3$ Receptor Antagonist: In Vitro and In Vivo Studies," *The Journal of Pharmacology and Experimental Therapeutics*, vol. 275, pp. 598–604 (1995).

J.W. Clitherow et al., "Novel 1,24–Oxadiazoles as Potent and Selective Histamine H$_3$ Receptor Antagonists," *Bioorganic and Medicinal Chemistry Letters*, vol. 6, pp. 833–838 (1996).

C.R. Ganellin et al., "Design of Potent Non–Thiourea H$_3$Receptor Histamine Antagonists," *Journal of Medicinal Chemistry*, vol. 38, pp. 3342–3350 (1995).

M. Misawa et al., "Pharmacological Studies on the Respiratory Tract (Rept. 186): The Effects of Histamine Receptor Antagonists on Guinea Pig Rhinitis Model," *Japanese Journal of Pharmacology*, vol. 64, No. S1, Abstract P–246 (1994).

C.J. Matson et al., "An Experimental Non–Invasive Animal Technique for Measuring Nasal Airway Resistance: I. Adrenergic and Antihistaminic Agents," *Archives Internationales de Pharmacodynamie et de Therapie*, vol. 232, pp. 68–78 (1978).

N. Sakai et al., "Effects of Thioperamide, a Histamine H$_3$ Receptor Antagonist, on Locomotor Activity and Brain Histamine Content in Mast Cell–Deficient W/W$^v$ Mice," *Life Sciences*, vol. 48, pp. 2397–2404 (1991).

F.E.R. Simons, "H$_1$–Receptor Antagonists: Clinical Pharmacology and Therapeutics," *Journal of Allergy and Clinical Immunology*, vol. 84, pp. 845–861 (1989).

A. Korte et al., "Characterization and Tissue Distribution of H$_3$ Histamine Receptors in Guinea Pigs by N$^\alpha$–Methylhistamine,"*Biochemical and Biophysical Research Communications*, vol. 168, pp. 979–986 (1990).

*Primary Examiner*—Leonard Schenkman
*Attorney, Agent, or Firm*—Robert A. Franks

[57] ABSTRACT

Relief from the symptoms of rhinitis is obtained by treatment with: (a) an antihistaminic effective amount of a histamine H$_1$ receptor antagonist; together with (b) a sufficient amount of a histamine H$_3$ receptor antagonist to provide a nasal decongestant effect. The components may be administered together in a single dosage form, or separately in the same or different dosage forms to maintain therapeutic systemic levels of both components.

8 Claims, No Drawings

TREATMENT OF UPPER AIRWAY ALLERGIC RESPONSES

This application claims benefit of provisional application 60/023,416 filed Aug. 16, 1996.

The present invention relates to a composition for treating allergy-induced responses in the mammalian airway, and to a method of treating allergy-induced airway responses.

Allergies are known to affect a very large fraction of the population. The allergic response in a particular individual may be caused by any of numerous environmental factors, some of which are consistently present and others being more seasonal in nature. Although not always recognized, worldwide losses in productivity due to allergic responses are economically very significant.

Clinical symptoms of seasonal allergic rhinitis typically include nasal itching and irritation, sneezing and watery rhinorrhea, frequently accompanied by nasal congestion. The perennial allergic rhinitis clinical symptoms are similar, except that nasal blockage may be more pronounced. Either type of allergic rhinitis may also cause other symptoms such as itching of the throat and/or eyes, epiphora and edema around the eyes. These symptoms may vary in intensity from the nuisance level to debilitating. Other types of rhinitis present the same types of symptoms.

At the cellular level, the mechanism of rhinitis has been the subject of considerable study. In addition to other processes, the mechanism is well known to involve the release of histamine [2-(4-Imidazolyl) ethylamine] which is synthesized and stored in secretory granules of mast cells located throughout the body, such as the skin, lungs, gut and the lining of blood vessels. Mast cell histamine is a mediator in immediate hypersensitivity reactions. Following its release from mast cells in the nasal mucosa, and acting primarily through histamine $H_1$ receptors, histamine evokes mucous secretion and vasodilatation, increases vascular permeability, induces pruritus and causes sneezing by sensory-nerve stimulation. The released histamine also can cause symptoms including hypotension, tachycardia, flushing and headache. Although histamine $H_2$ receptors (which typically activate to increase gastric acid secretion) may also be involved in the allergic response, their effects are not presently considered to be significant.

Histamine $H_3$ receptors are found on sympathetic nerves, where they modulate sympathetic neurotransmission and attenuate a variety of end organ responses under control of the sympathetic nervous system. Specifically, $H_3$ receptor activation by histamine attenuates norepinephrine outflow to resistance and capacitance vessels, causing vasodilatation.

It is thought that the primary symptoms of rhinitis involve activity at $H_1$ receptors. Indeed, relief has been provided since the 1940's by a succession of "antihistamine" $H_1$ receptor antagonists including the well-known drug chlorpheniramine maleate. More recently developed drugs provide $H_1$ receptor antagonist activity with lower levels of undesirable side effects, among the most noteworthy being greatly reduced incidences of somnolence and anticholinergic effects. This is considered to result from the later drugs' greater selectivity for $H_1$ receptors, as well as their reduced ability to cross the blood-brain barrier. In general, none of the $H_1$ receptor antagonists are known to have significant effects on $H_2$ or $H_3$ receptors.

$H_1$ receptor antagonists have been proven efficacious for preventing and relieving sneezing, itching, rhinorrhea and other symptoms of the early allergic response, but have not been found to be very effective for relief of the nasal blockage which is characteristic of the later stages of an allergic reaction. Thus, it has been common to concurrently administer sympathomimetic amine decongestant drugs, such as phenylpropanolamine or pseudoephedrine which function as α-adrenoceptor agonists; several combination products containing both $H_1$ receptor antagonists and sympathomimetic amine decongestants are commercially available. However, not all allergy sufferers should use these decongestants drugs, due to their frequently observed central nervous system and cardiovascular side effects which include agitation, sleeplessness, tachycardia, angina pectoris and hypertension.

U.S. Pat. Nos. 5,217,986 and 5,352,707 to Pomponi et al. attribute an ability for treating conditions including rhintitis and airway congestion to certain compounds apparently having $H_3$ receptor binding activity, but no $H_1$ receptor antagonist activity. However, no clinical observation or other support is provided for this proposition.

It would be desirable to have available a treatment for allergic rhinitis which provides relief from all of the common symptoms thereof, including nasal congestion, but which does not exhibit adverse nervous system or cardiovascular effects.

SUMMARY OF THE INVENTION

The invention is a composition for the treatment of the symptoms of allergic rhinitis, comprising a combination of at least one histamine $H_1$ receptor antagonist and at least one histamine $H_3$ receptor antagonist. Also included within the invention is a method for treating symptoms of allergic rhinitis, comprising maintaining in the circulatory system an antihistaminic amount of at least one histamine $H_1$ receptor antagonist, together with sufficient amounts of at least one histamine $H_3$ receptor antagonist to provide a nasal decongestant effect.

DETAILED DESCRIPTION OF THE INVENTION

For purposes of the present invention, an "antihistaminic" effect will be considered that symptomatic relief which has classically been considered as being obtainable by a sufferer of rhinitis, resulting from the administration of $H_1$ receptor antagonists, e.g., without limitation thereto, attenuation of sneezing, ocular and nasal itching, rhinorrhea and epiphora. This antihistaminic effect specifically does not include significant relief from nasal congestion symptoms.

Numerous chemical substances are known to have histamine $H_1$ receptor antagonist activity. Many useful compounds can be classified as ethanolamines, ethylenediamines, alkylamines, phenothiazines or piperidines. Representative $H_1$ receptor antagonists include, without limitation: astemizole, azatadine, azelastine, acrivastine, brompheniramine, chlorpheniramine, clemastine, cyclizine, carebastine, cyproheptadine, carbinoxamine, descarboethoxyloratadine (also known as SCH-34117), doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, picumast, pyrilamine, promethazine, terfenadine, tripelennamine, temelastine, trimeprazine and triprolidine. Other compounds can readily be evaluated to determine activity at $H_1$ receptors by known methods, including specific blockade of the contractile response to histamine of isolated guinea pig ileum.

The currently known histamine $H_3$ receptor antagonists cannot be easily classified chemically, but include, without limitation: thioperamide, impromidine, burimamide, clobenpropit, impentamine, mifetidine, S-sopromidine, R-sopromidine, 3-(imidazol-4-yl)-propylguanidine (SKF-91486), 3-[(4-chlorophenyl)methyl]-5-[2-(1H-imidazol-4yl)ethyl] 1,2,3-oxadiazole (GR-175737), 4-(1-cyclohexylpentanoyl-4-piperidyl) 1H-imidazole (GT-2016), 2-{[2-[4(5)-imidazolyl]ethyl]thio}-5-nitropyridine (UCL-1199) and clozapine. Other compounds can readily be evaluated to determine activity at $H_3$ receptors by known methods, including the guinea pig brain membrane assay and the guinea pig neuronal ileum contraction assay, both of which are described in U.S. Pat. No. 5,352,707. Another useful assay utilizes rat brain membranes and is described by West et al., "Identification of Two $H_3$-Histamine Receptor Subtypes," *Molecular Pharmacology*, Vol. 38, pages 610–613 (1 990).

A particularly useful screening assay measures binding to sites in guinea pig brain membranes. This test is described in detail by Korte et al., "Characterization and Tissue Distribution of $H_3$ Histamine Receptors in Guinea Pigs by $N^\alpha$-Methylhistamine," in *Biochemical and Biophysical Research Communications*, Vol. 168, pages 979–986 (1990), and quantifies the displacement of bound radiolabeled $N^\alpha$-methylhistamine from tissues by candidate compounds. Results are expressed as "$K_i$" values, in nanoMolar (nM) units, which values can be considered as being dissociation constants for the $H_3$ antagonist on the $H_3$ receptor system, or an index of antagonist affinity for the receptor. The present inventors have evidence that decongestant activity in their invention for a given $H_3$ antagonist concentration can be predicted to increase as the $K_i$ value obtained from the assay for an antagonist decreases. In general, $K_i$ values less than about 200 nM are considered necessary for an agent to be useful as an $H_3$ antagonist in the invention. More preferably, the agent will exhibit $K_i$ values of 100 nM or less.

Any of the foregoing drugs may be used in the form of a pharmaceutically suitable salt, ester or other form, where solubility or other characteristics of the drug should desirably be modified, such as for formulation convenience.

While it is not desired to be bound to any particular theory of operation, it is normally expected that sympathetic innervation of airway blood vessels leads to vasoconstriction, which would oppose airway resistance and congestion. However, during conditions of mast cell activation and the release of histamine, such as in allergic diseases, the released histamine acts on $H_3$ receptors located on sympathetic nerve terminals to inhibit sympathetic neurotransmission and opposes the decongestant effect of norepinephrine, as well as activating $H_1$ receptors that produce other symptoms of allergic diseases.

Antihistamines that block $H_1$ receptors do not antagonize the $H_3$ receptor-mediated inhibition of norepinephrine release and, therefore, are generally without activity against the effects of histamine in promoting airflow limitation and congestion.

The decongestant effect of the combination of the present invention is thought to reside in the anti-$H_3$ activity which enhances the release of norepinephrine, a natural endogenous decongestant, at the site of congestion in the nose, but not elsewhere in the body, so no systemic cardiovascular effects are observed. The antiallergic effects reside primarily in the anti-H, activity of the treatment.

Amounts of $H_1$ receptor antagonists and $H_3$ receptor antagonists which are administered to achieve antihistaminic and decongestant effects will vary, depending on the activities of the exact compounds used. In general, between about 1 and about 1000 milligrams of each compound will be administered in a dose. The compounds may be combined in a single dosage formulation, or may be administered in separate dosage forms, and these may be solid (such as tablets, capsules, sachets and the like), liquid (such as solutions or suspensions) or inhalation aerosols for either or both compounds. While the solid compounds will typically be administered orally, the liquids may be administered orally or by injection. Other dosage forms, such as suppositories, are also useful.

Appropriate amounts of the $H_1$ receptor antagonists and $H_3$ receptor antagonists for each dose, and the proper dosing regimen, must be determined for each combination by suitable clinical trials. Ideally, each drug will have a similar duration of action after dosing, frequently indicated by elimination half-life and by clinical observation of symptom relief. However, in the event that the individual drug duration of action is considerably different for members of a given combination, it will be necessary to resort to alternate formulation techniques, such as inhibiting the release kinetics of a component from the formulation to prolong its activity. These techniques are well known in the pharmaceutical formulation art. The least expensive dosing regimen, however, may involve separately administering the $H_1$ and $H_3$ receptor antagonists, using dose frequencies and strengths as necessary to maintain therapeutic systemic levels of both agents.

The invention will be further described by means of the following examples, which are not intended to limit the scope of the claimed invention in any manner. In the examples, compositional percentages are weight percentages, unless the context clearly indicates otherwise.

EXAMPLE 1

An objective measurement of nasal airway resistance to air flow is used to demonstrate the induction and relief of nasal congestion..

Adult cats are anesthetized with intraperitoneal injections of sodium pentobarbital. The right femoral artery and vein are cannulated for measurement of blood pressure with a pressure transducer, and for the administration of drugs. The animals are paralyzed with intravenous gallamine triethiodide and subsequently mechanically ventilated with room air, using an animal ventilator. After isolation of the cervical esophagus, a cuffed endotracheal tube is advanced rostrally into the posterior nasopharynx and inflated to form an air-tight seal, allowing continuous measurement of pressure changes within the nasal cavity. The right nasal airway is occluded with dental impression compound, and humidified air is passed through the left nasal airway at about 1.7 liters per minute. By means of pressure transducers, nasal airway pressure and insufflation pressure can be derived and electronically recorded.

Nasal airway resistance (N is determined by dividing the pressure within the nasal cavity (expressed in centimeters of water) by the air flow rate (expressed in liters per minute). Measurements with 18 subject animals yield an average baseline NAR of 2.6.

The known histamine releaser "Compound 48/80" (the condensation product of N-methyl-p-methoxyphenethylamine with formaldehyde, sold by Sigma Chemical Company, St. Louis, Mo., USA), as a 1.0 percent solution in 0.9 percent aqueous saline solution, is aerosolized into the air stream for 2 minutes to induce an increased NAR. This effect is used to study the decongestant effects of various test substances, administered to the animals intravenously 10 minutes prior to the introduction of Compound 48/80. These substances include 0.9 percent aqueous saline (normal saline "Vehicle"), phenylpropanolamine hydrochloride at 1.0 mg/Kg of the free drug, thioperamide maleate at 10 mg/Kg of the free drug and chlorpheniramine maleate at 0.8 mg/Kg of the free drug, all of the drug compounds being in solution in 0.9 percent aqueous saline.

Results are obtained, as shown below:

| Treatment | NAR |
|---|---|
| Vehicle | 9.1 |
| Thioperamide | 6.7 |
| Chlorpheniramine | 6.0 |
| Phenylpropanolamine | 2.9 |

It can be seen that the sympathomimetic amine significantly prevents congestion, but the $H_1$ and $H_3$ receptor antagonists, administered singly, are decidedly inferior at preventing nasal congestion. Only the phenylpropanolamine gives a statistically different result from that for the vehicle.

EXAMPLE 2

The experiment of the preceding example is repeated, but the intravenous drugs are varying amounts of thioperamide (administered as the maleate), in solution together with a constant 0.8 mg/Kg of chlorpheniramine ("CPA," administered as the maleate).

Results are obtained, as shown below:

| Treatment | NAR |
|---|---|
| Vehicle | 9.1 |
| Thioperamide 1.0 mg/Kg + CPA | 6.1 |
| Thioperamide 3.0 mg/Kg + CPA | 4.3 |
| Thioperamide 10 mg/Kg + CPA | 2.2 |

There is a significant congestion prevention response to increasing doses of thioperamide in the presence of chlorpheniramine, although the combination of 1 mg/Kg thioperamide and 0.8 mg/Kg chlorpheniramine is not statistically different from the vehicle. Comparison of the maximum response results shown in this example, to the results in Example 1 for administration of 1.0 mg/Kg phenylpropanolamine, indicates that the combination of 0.8 mg/kg chlorpheniramine and 10 mg/Kg thioperamide is at least as effective at preventing nasal congestion.

EXAMPLE 3

The experiment of preceding Example 1 is repeated, but the intravenous drug administered is clobenpropit in varying amounts, either alone or in solution together with a constant 0.8 mg/Kg of chlorpheniramine ("CPA," administered as the maleate).

Results are obtained, as shown below:

| Treatment | NAR |
|---|---|
| Vehicle | 9.1 |
| Clobenpropit 1.0 mg/Kg | 5.5 |
| Clobenpropit 0.3 mg/Kg + CPA | 2.9 |
| Clobenpropit 1.0 mg/Kg + CPA | 3.4 |

Clobenpropit alone does not exhibit significant prevention of nasal congestion, but the combinations of clobenpropit and chlorpheniramine are effective to prevent congestion. The results for 0.3 and 1.0 mg/Kg clobenpropit, administered together with 0.8 mg/Kg chlorpheniramine, are statistically different from those for the vehicle.

EXAMPLE 4

Blood pressure data from the experiments of the preceding examples are examined, to determine the effects of certain congestion-preventing treatments. These data are as shown below, wherein the change from baseline is shown for various drugs ("CPA" being chlorpheniramine, administered as the maleate):

| Treatment | mm Hg |
|---|---|
| Vehicle | −16 |
| Thioperamide 10 mg/Kg + CPA 0.8 mg/kg | −10 |
| Phenylpropanolamine 1 mg/Kg | +31 |

The data show that treatment with the thioperamide and chlorpheniramine combination has little adverse effect on blood pressure, while the phenylpropanolamine treatment (which yields an approximately equivalent nasal congestion-preventing effect) significantly increases blood pressure. Only the results for phenylpropanolamine are statistically different from those for the vehicle.

EXAMPLE 5

The affinity of various histamine $H_3$ receptor antagonists for binding sites is determined by a guinea pig brain membrane assay, according to the procedure of Korte et al., *Biochemical and Biophysical Research Communications*, Vol. 168, pages 979–986 (1990).

Results are as shown below:

| Compound | $K_i$, nM |
|---|---|
| Verongamine | 280 |
| Thioperamide | 12 |
| Clobenpropit | 0.1 |

These results predict that verongamine, having a $K_i$ value higher than 200 nM, will not be useful in the practice of the invention.

To test the statement in U.S. Pat. No. 5,217,986 that verongamine itself has decongestant activity, an experiment similar to that of preceding Example 1, but with a different vehicle, is conducted. The following results are obtained:

| Treatment | NAR |
|---|---|
| Vehicle | 7.8 |
| Verongamine 10 mg/Kg | 7.3 |

Contrary to the prediction of the patent, the result for verongamine is not statistically different from that for the vehicle.

EXAMPLE 6

The experiment of preceding Example 3 is conducted, using loratadine as the antihistaminic compound at 3 mg/Kg, administered in a solution ("Vehicle") which is 30 percent Dimethylsulfoxide, 40 percent Ethanol and 30 percent normal saline, and using thioperamide as the $H_3$ receptor antagonist at 10 mg/Kg.

Results are obtained, as follows:

| Treatment | NAR |
|---|---|
| Vehicle | 12.6 |
| Loratadine | 10.2 |
| Loratadine + Thioperamide | 2.1 |

Only the results for the combination of loratadine and thioperamide are statistically different from those for the vehicle.

EXAMPLE 7

The experiment of the preceding example is repeated, using 1 mg/Kg descarboethoxyloratadine as the histamine $H_1$ antagonist. Similar results are obtained.

EXAMPLE 8

Tablets containing a combination of $H_1$ receptor antagonist and $H_3$ receptor antagonist are prepared by combining the following ingredients (per tablet to be prepared):

$H_1$ antagonist effective amount $H_3$ antagonist effective amount

Lactose 100 mg

Corn starch, 10% paste 5 mg

Corn starch, dried 25 mg

Magnesium stearate 1.25 mg

The first, second, third, and a portion of the fifth, ingredients are thoroughly blended in a suitable mixer for at least 10–15 minutes. The mixture is granulated with the fourth ingredient and, if necessary, passed through a sieve having openings about 0.6 mm. After drying, the granules are mixed with the sixth ingredient and the remaining portion of the fifth ingredient in a mixer until uniform and compressed into tablets of a desired shape in a tablet press, using suitable dies. If desired, the tablets may be coated, such as with sugar and/or with a wax.

EXAMPLE 9

Capsules containing a combination of $H_1$ receptor antagonist and $H_3$ receptor antagonist are prepared by combining the following ingredients (per capsule to be prepared):

$H_1$ antagonist effective amount $H_3$ antagonist effective amount

Lactose 125 mg

Corn starch, dried 25 mg

Magnesium stearate 2.5 mg

The first four ingredients are mixed thoroughly in a suitable mixer for 10–15 minutes, then the fifth ingredient is added and mixing continued for another 5 minutes. Predetermined amounts of the mixture are filled into two-piece hard gelatin capsules of appropriate size.

EXAMPLE 10

A parenteral solution formulation is prepared by dissolving effective amounts of the $H_1$ receptor antagonist and $H_3$ receptor antagonist sterile powders in sterile water for injection, U.S.P. or bacteriostatic water for injection, U.S.P. Suitable pH buffers and/or preservatives may be added, as needed.

EXAMPLE 11

An oral liquid is prepared by dissolving and/or suspending effective amounts of an $H_1$ receptor antagonist and an $H_3$ receptor antagonist in a solution made from water, containing desired amounts of the following safely ingestible ingredients: sweetening agents, flavorants, colorants, vegetable oil and suspending agents and/or thickeners.

It should be noted that, in any of the formulations of preceding Examples 8–1 1, either of the $H_1$ receptor antagonist or the $H_3$ receptor antagonist can be omitted if the active compounds are to be separately administered. It is not necessary to administer the drugs in the same dosage forms.

What is claimed is:

1. A method of relieving symptoms of rhinitis in a mammal, comprising simultaneously maintaining in the circulatory system: (a) an antihistaminic effective amount of one or more histamine $H_1$ receptor antagonists; and (b) a sufficient amount of one or more histamine $H_3$ receptor antagonists having a $K_i$ value less than about 200 nanoMolar in a guinea pig brain membrane assay to provide a nasal decongestant effect.

2. The method of claim 1, wherein the $H_1$ receptor antagonist and the $H_3$ receptor antagonist are present in a single dosage form.

3. The method of claim 1, wherein the $H_1$ receptor antagonist and the $H_3$ receptor antagonist are administered in separate dosage forms.

4. The method of claim 1, wherein the histamine $H_1$ receptor antagonist is selected from the group consisting of astemizole, azatadine, azelastine, acrivastine, brompheniramine, chlorpheniramine, clemastine, cyclizine, carebastine, cyproheptadine, carbinoxamine, descarboethoxyloratadine, doxylamine, diphenhydramine, cetirizine, dimenhydrinate, dimethindene, ebastine, epinastine, efletirizine, fexofenadine, hydroxyzine, ketotifen, loratadine, levocabastine, mizolastine, mequitazine, mianserin, noberastine, meclizine, norastemizole, picumast, pyrilamine, promethazine, terfenadine, tripelennamine, temelastine, trimeprazine, triprolidine and mixtures of any two or more of the foregoing.

5. The method of claim 1, wherein the histamine $H_3$ receptor antagonist is selected from the group consisting of thioperamide, impromidine, burimamide, clobenpropit, impentamine, mifetidine, S-sopromidine, R-sopromidine, SKF-91486, GR-175737, GT-2016, UCL-1 199, clozapine and mixtures of any two or more of the foregoing.

6. The method of claim 1, wherein the histamine $H_1$ receptor antagonist comprises loratadine.

7. The method of claim 1, wherein the histamine $H_1$ receptor antagonist comprises descarboethoxyloratadine.

8. The method of claim 1, wherein the histamine $H_3$ receptor antagonist has a $K_i$ value not exceeding about 100 nanoMolar.

* * * * *